United States Patent [19]

Wiggins

[11] Patent Number: 5,038,763

[45] Date of Patent: Aug. 13, 1991

[54] KNEE BRACE

[76] Inventor: Christopher N. Wiggins, 8083 Mariners Dr., #1302, Stockton, Calif. 95209

[21] Appl. No.: 408,127

[22] Filed: Sep. 15, 1989

[51] Int. Cl.⁵ ............................ A61F 5/00; A61F 5/01
[52] U.S. Cl. .................................. 128/80 C; 128/88; 128/80 R; 623/39
[58] Field of Search .................. 128/80 C, 80 F, 88, 128/77, 87 R, 80 R, 80 H; 2/22, 24; 623/39

[56] References Cited

U.S. PATENT DOCUMENTS

| | | | |
|---|---|---|---|
| 4,493,316 | 1/1985 | Reed et al. | 128/80 C |
| 4,502,472 | 3/1985 | Pansiera | 128/80 F |
| 4,554,913 | 12/1985 | Womack et al. | |
| 4,633,867 | 1/1987 | Kausek et al. | |
| 4,697,583 | 10/1987 | Mason et al. | |
| 4,715,363 | 12/1987 | Detty | |
| 4,726,362 | 2/1988 | Nelson | |
| 4,733,656 | 3/1988 | Marquette | 2/22 |
| 4,768,500 | 9/1988 | Mason et al. | 128/88 |

Primary Examiner—Richard J. Apley
Assistant Examiner—Lynne A. Reichard
Attorney, Agent, or Firm—Majestic, Parsons, Siebert & Hsue

[57] ABSTRACT

This invention relates to a knee support device which enables a knee brace to track closely the movement of the tibia. In use, a complete knee brace comprises two of the knee support devices of this invention, one on each side of the leg. The knee support device comprises an upper and a lower elongated brace member releasably secured to a person's thigh and leg, respectively. Each of the two brace members includes pivot means and gear means, such that the gear means of the two brace members engage each other to rotate each brace member about the pivot means of the corresponding member. The upper and lower brace members on each side of the leg are connected by a link member connecting the pivot means of the two braces. The means for securing the brace members to the leg are placed such that the pivots are anterior to the knee joint, so that the rotation of the lower brace member tracks the tibia in flexion when the person and the brace members are viewed in profile. The link member and portions of the brace members remain close to the knee joint when it is bent to provide greater support and protection for the joint.

5 Claims, 4 Drawing Sheets

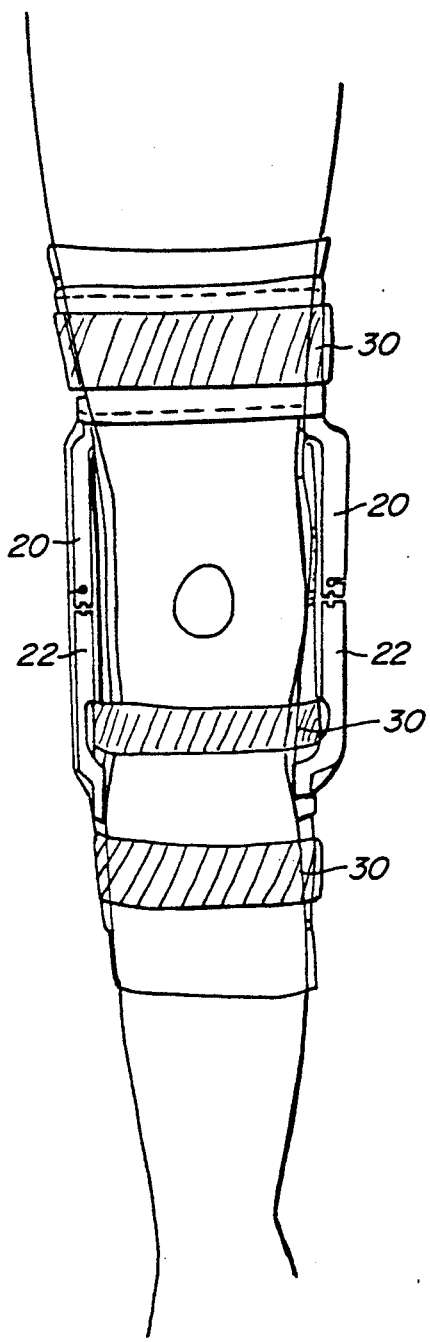
FIG._1.
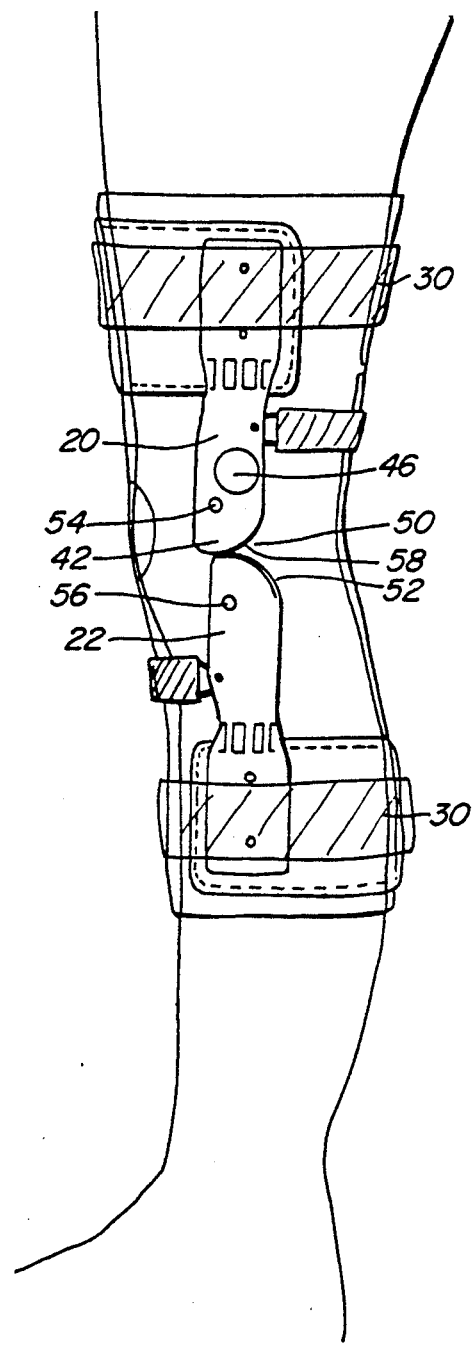
FIG._2.

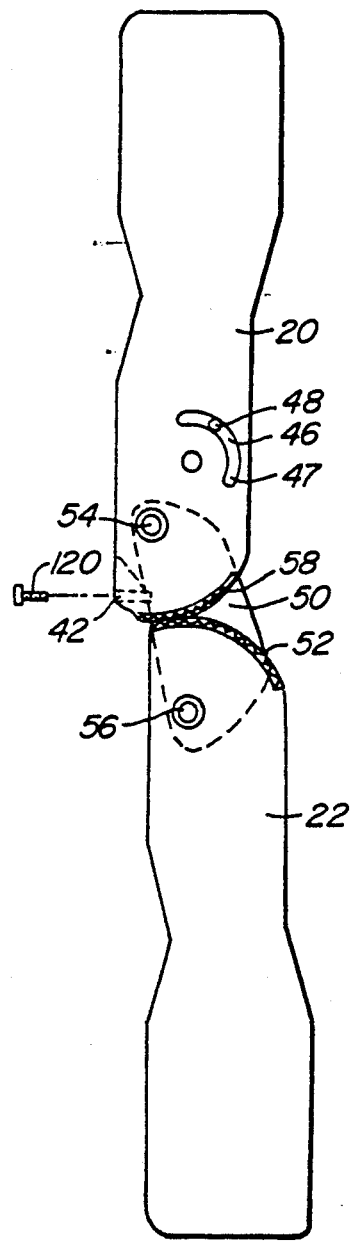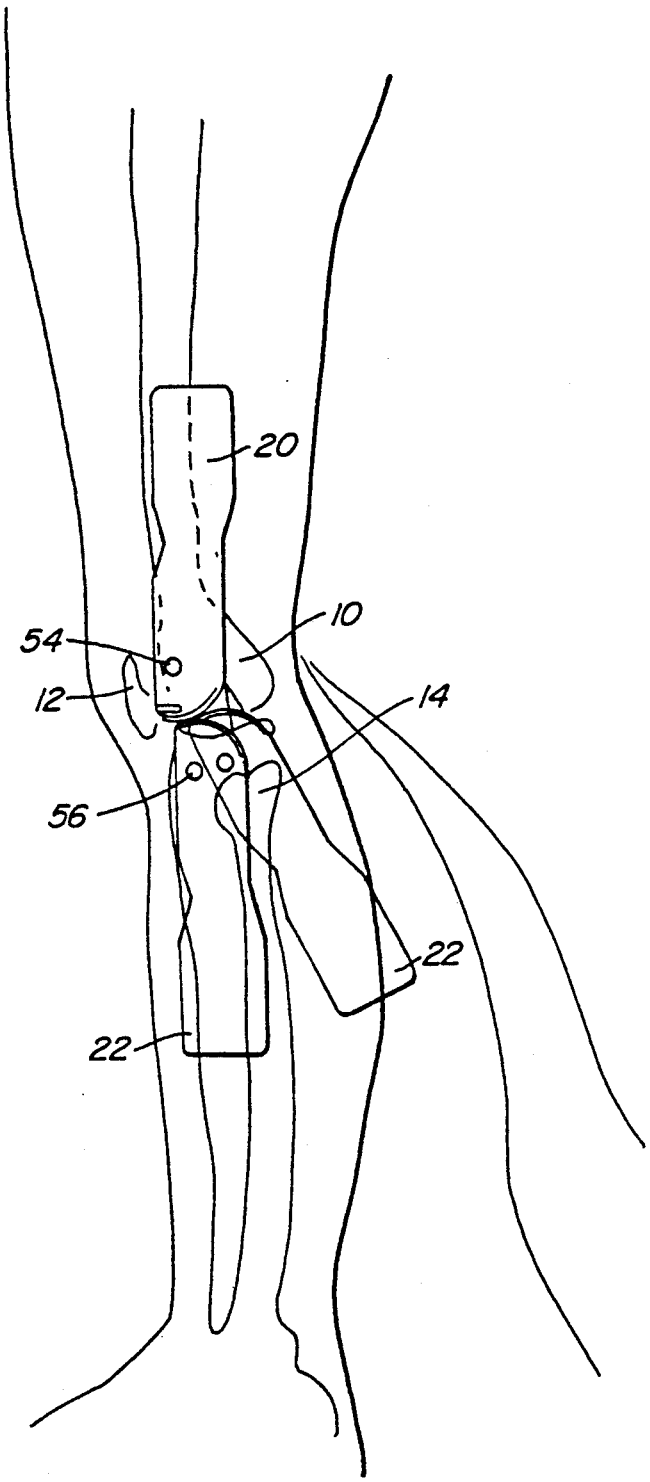
FIG._3.
FIG._4.

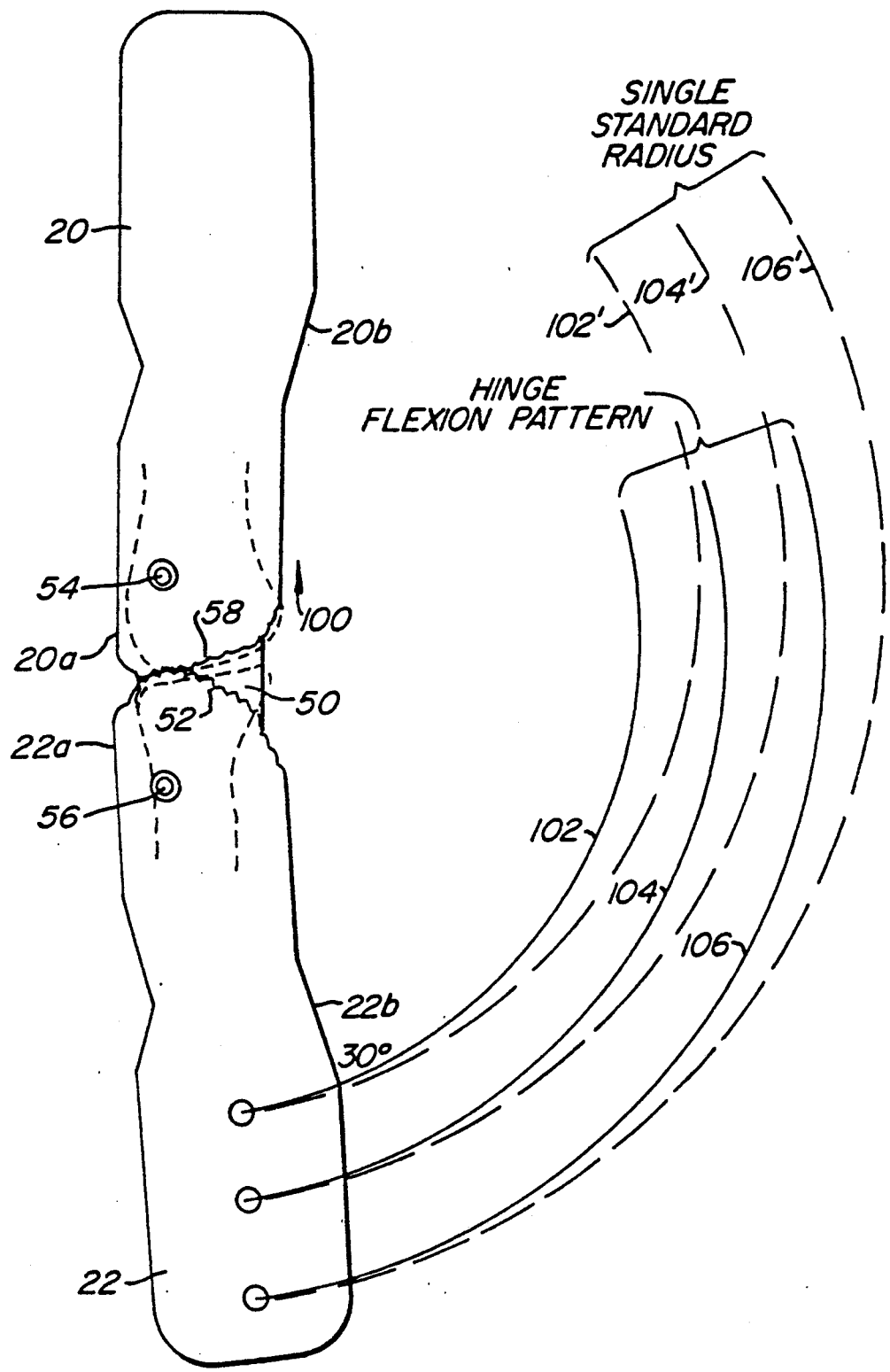
FIG._5.

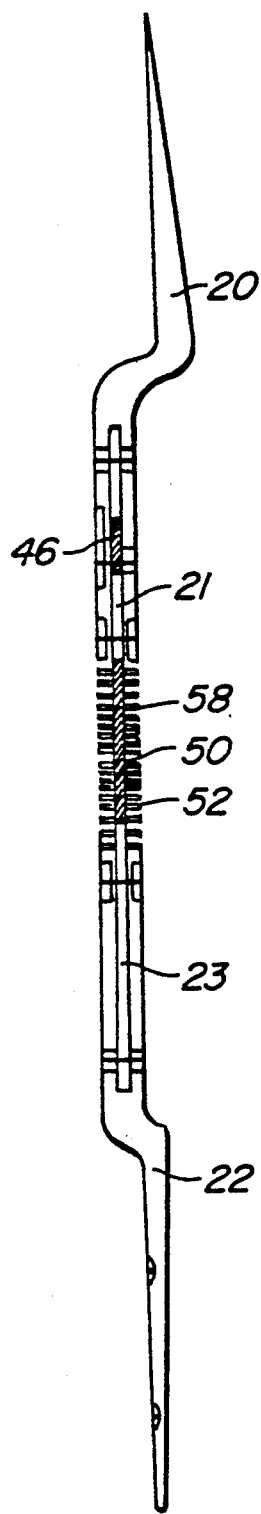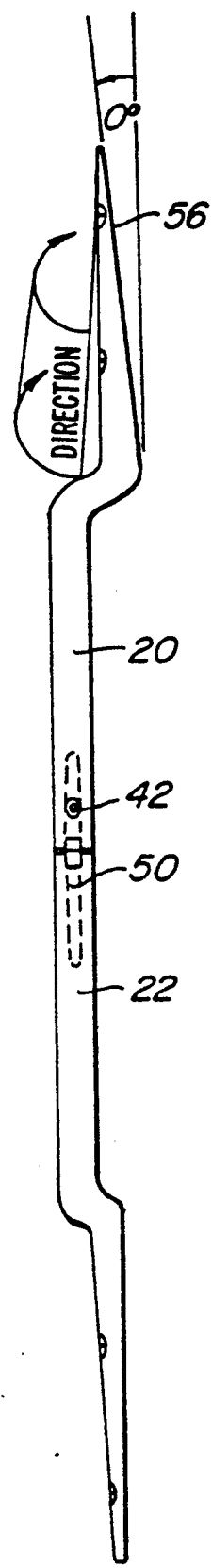
FIG._6.  FIG._7.

KNEE BRACE

BACKGROUND OF THE INVENTION

This invention relates in general to orthopedic braces and in particular to an improved injury preventing and post-injury rehabilitative knee brace.

One of the areas of the body most vulnerable to athletic injuries is the knee. Many serious injuries result from hyperextension of the knee. Other injuries result from medial and lateral twisting movements of the knee joint.

The purpose of a knee brace is to provide exterior support for the knee to prevent unnatural movements of the knee joint which could injure or reinjure the knee ligaments or cartilage, while allowing normal movement of the knee joint. Various types of knee braces have been developed in an attempt to protect the knee against unnatural medial and lateral movements and hyperextension. A knee brace is typically worn by a person who has a pre-existing condition, both before and after knee surgery. Knee braces are also worn by persons with minor instabilities, and by persons engaged in sports activities, to prevent knee injuries.

Many braces are disclosed in the patent literature and many are available commercially. Examples of prior art knee joint braces are as follows: U.S. Pat. Nos. 4,697,538 (Mason, et al.); 4,715,363 (Detty); and 4,726,362 (Nelson).

Mason discloses a knee brace for externally replacing the function of a torn anterior cruciate ligament. It discloses an anterior thigh cuff and a posterior calf cuff to apply a differential force couple forwardly to the femur and rearwardly to the tibia to serve the anterior cruciate ligament function. Bicentric geared hinges are used on both the lateral and medial sides of the knee to achieve the necessary leverage.

Nelson discloses a knee brace and wrap assembly using a three-point hinge mechanism to connect the upper and lower leg supports which are fastened to only the exterior sides of the thigh and calf. The leg supports and hinge assembly restrict extension of the leg at the knee joint.

Detty discloses a knee brace comprised of elongated brace members connected by polycentric hinges. A set of pairs of wedge-like stop members are releasably secured to associated brace members adjacent the hinges to serve as a stop means to limit the angle of extension.

However, each of these knee braces has numerous disadvantages that are overcome by the present invention.

SUMMARY OF THE INVENTION

It is an object of this invention to provide a knee brace which enables the brace to track closely the movement of the tibia. Another object of this invention is to provide a knee brace which can be adjusted readily to limit both the maximum extension and the maximum flexion angles permitted by the brace. A further object of the invention is to provide a knee brace which reduces pistoning forces on the knee.

In use, a complete knee brace comprises two of the knee support devices of this invention, one on each side of the leg. The knee support device comprises an upper and a lower elongated brace member releasably secured to a person's thigh and leg, respectively. Each of the two brace members includes pivot means and gear means, such that the gear means of the two brace members engage each other to rotate each brace member about the pivot means of the corresponding member.

The upper and lower brace members on each side of the leg are connected by a link member connecting the pivot means of the two braces. The means for securing the brace members to the leg are placed such that the pivots are anterior to the knee joint, so that the rotation of the lower brace member tracks the tibia in flexion when the person and the brace members are viewed in profile. The link member and portions of the brace members remain close to the knee joint when it is bent to provide greater support and protection for the joint.

These and other objects and advantages of the present invention will be better understood and appreciated from the following detailed description of the drawings.

BRIEF DESCRIPTION OF THE DRAWINGS

FIG. 1 is an anterior view of the leg, showing the complete knee brace consisting of two knee support devices in position on the leg.

FIG. 2 is a lateral view of the leg, showing the knee brace in profile, consisting of one knee support device in position on the leg.

FIG. 3 shows a side view of the two brace members connected by the link plate and a cutaway view of the extension stop means.

FIG. 4 shows a lateral view of the knee support device on a leg in both flexed and extended positions, with dotted lines showing the orientation of the femur, tibia and patella.

FIG. 5 is a schematic side view showing the location of the knee support device relative to the femur and tibia and the hinge flexion pattern.

FIG. 6 is a posterior edge view of the knee support device, showing the flexion and extension adjustment means.

FIG. 7 is an anterior edge view of the knee support device, showing the definition of the dihedral angle of the upper member.

DETAILED DESCRIPTION OF THE PREFERRED EMBODIMENTS

As shown in FIG. 1, a complete knee brace using the present invention includes two of the knee support devices shown in FIG. 2, each knee support device comprising an upper elongated brace member 20, a lower elongated brace member 22, a link member 50 for connecting the two brace members in a hinged relationship and means 30 for releasably securing the upper and lower brace members to the person's thigh and calf respectively. This configuration keeps the knee support device close to the knee joint when it is bent, so that support and protection of the knee joint are provided.

The structure of the hinged relationship in the preferred embodiment is shown in FIGS. 1–4. The hinged relationship enables the rotation of the lower brace member 22 to track the movement of the tibia in flexion. The upper brace member 20 includes a pivot 54 and the lower brace member 22 includes a pivot 56. The link member 50 is a substantially trapezoidal metal plate connecting the pivot 54 of the upper brace member 20 to the pivot 56 of the lower brace member 22 to form the knee support device seen in FIG. 2. In this arrangement the link member 50 maintains a substantially constant distance between the two pivot means when the lower member 22 is rotated relative to the upper member 20.

When viewed in position on the leg, the brace members 20, 22 each have a proximal end nearer the knee joint and a distal end farther from the knee joint. The brace members are each plates in which the proximal end has a slot therein. As seen in FIGS. 3 and 6, the link member 50 is a plate that fits inside the slot 21 of the upper brace member 20 and the slot 23 of the lower brace member 22 so that the proximal ends of the two brace members, together with the portions of the link members inside the respective slots in the proximal ends, form two sandwich configurations. Together the link and brace members increase the torsional rigidity of the area of the knee supported at the junction of the two brace members and the link member. This support is especially advantageous to avoid injury during flexion of the knee.

Each brace member also includes sector gear means such that the gear teeth 58 of the upper brace member 20 are adapted to engage the gear teeth 52 of the lower brace member 22, so that each gear rotates about the pivot means of its respective member. The gears 52 and 58 remain engaged when rotated about their respective pivot means in order to rotate the brace members relative to each other.

The location of the gears and the pivots on the brace members is a significant feature of the device. In both the upper brace member 20 and the lower brace member 22, the gear teeth are located at the proximal end of each member and centered on the pivot of that member. The pivots 54, 56 are located closer to the anterior than to the posterior sides of the respective brace members. As seen in FIG. 4, the pivots 54, 56 of both brace members remain positioned anterior to the knee joint in both extension and flexion, thus providing improved stability and support while allowing normal motion.

As clearly shown in FIG. 5, pivots 54, 56 are located anterior to the knee joint when the knee brace device of this invention is in place to protect and assist a person's knee. With this arrangement, the distance between the distal end of the lower brace member and the pivot of the upper brace member decreases as the knee is bent in flexion.

As also shown in FIG. 5, when the knee is bent in flexion, the end of the tibia at the knee joint follows path 100. By locating pivots 54, 56 anterior to the knee joint, the movement of the lower brace member 22 follows the shape of path 100, as illustrated by paths 102, 104, 106 of the distal end of member 22 in FIG. 5. This arrangement gives greater stability than found in the prior art, where the rotation pattern is depicted by the paths 102', 104', 106', representing the radii of motion about a single pivot.

In the preferred embodiment shown in FIG. 5, the members 20, 22 are attached to the thigh and leg in such relative position that they overlap the femur and tibia when viewed laterally as shown in FIG. 5 to lend maximum support to the knee. Pivots 54, 56 are located closer to the anterior edges 20a, 22a than to posterior edges 20b, 22b to achieve the arrangement wherein the pivots are anterior to the knee joint. It will be understood, however, that other arrangement are possible. All such variations are within the scope of the invention.

The configuration of FIG. 5 allows a maximum rotation of the tibia about the knee joint in flexion of about 125 degrees, which is the normal range of motion for a healthy knee. The decrease in distance between the distal end of the lower brace member 22 and the pivot 54 of the upper brace member 20 for the last 90 degrees is greater than that of the first 35 degrees. The device can therefore be worn for preventive use in sports, since it permits normal flexion movements while providing lateral support against twisting.

Referring to FIG. 7, the distal end of the upper brace member 20 is at an angle to the plane of the lower brace member 22, defining a dihedral angle 56. The dihedral angle conforms to the shape of the thigh and reduces pistoning forces on the knee. The most effective angle has been found to be approximately ten degrees.

Another novel feature of this device is a stop means 50 attached to the upper brace member that engages the link member to prevent hyperextension of the knee joint. As seen in the cutaway portion of FIG. 3, the stop means is a screw 120 set in a threaded hole 42 that opens to the anterior side of the upper brace member 20 and runs through to the interior surface of the slot 21 of the same member, as seen in FIG. 6. The set screw 120 can be adjusted from the anterior side to increase or decrease the length of the screw which protrudes into the inner slot 21, so as to restrict movement of the link member 50. In this way, the maximum angle of extension can be easily changed.

A second stop means is provided to limit flexion. A cam 46 is provided in the upper brace member that can be adjusted to engage the link member at different points in its rotation. The cam is slidably engaged in a semi-circular slot 47 in the upper brace member. By means of a screw 48 inserted into the slot, the cam 46 can be adjusted relative to the slot 47, thereby changing the range of motion of the link member 50 and the range of motion of the lower brace member 22.

While the present invention has been particularly described with reference to FIGS. 1-7, it should be understood that the specific embodiments are for illustration only and should not be taken as limitations upon the invention. It is contemplated that many changes and modifications may be made by one of ordinary skill in the art without limiting the scope of the invention as disclosed above.

What is claimed is:

1. A knee support device, comprising:
    an upper elongated brace member to be releasably secured to a person's thigh;
    a lower elongated brace member to be releasably secured to a person's leg;
    each of the two brace members including pivot means and gear means, wherein the gear means of the two brace members are adapted to engage each other to each rotate about the pivot means of the corresponding member;
    a link member connecting the pivot means of the two braces and maintaining a substantially constant distance between said pivot means when the lower member is rotated relative to the upper member, so that the gear means of the two member also remain engaged when rotated about the pivot means in order to rotate the brace members relative to each other; and
    means for securing the upper and lower brace members respectively to a person's thigh and leg, said pivot means of the members being anterior to the knee joint of the person when said two brace members are so secured and when the person and the brace members are viewed in profile, so that the rotation of the lower brace member tracks the movement of the tibia in flexion and so that the link member and portions of the brace members remain close to the knee joint when it is bent to provide greater support and protection of the knee joint;

said device further comprising stop means attached to one of the brace members for engaging the link member to prevent hyperextension.

2. The device of claim 1, wherein the brace members are each plates, one end of each brace member having a slot therein on the posterior side forming a sandwich configuration, wherein the link member is a plate and fits inside the slots of the two brace members, said pivot means of each of the two brace members connecting the brace members to the link member at said sandwich configuration, wherein said stop means comprises a surface of the slot at the anterior side of the upper member and facing the link member.

3. The device of claim 2, said stop means further comprising a screw which is threadably engaged with the surface of the slot at the anterior side of the upper member for engaging the link member.

4. The device of claim 3, wherein the position of the screw relative to the link member is adjustable by turning the screw relative to the anterior side of the upper brace member to adjust the angle of extension permitted for a knee.

5. A knee support device, comprising:

an upper elongated brace member to be releasably secured to a person's thigh;

a lower elongated brace member to be releasably secured to a person's leg;

each of the two brace members including pivot means and gear means, wherein the gear means of the two brace members are adapted to engage each other to each rotate about the pivot means of the corresponding member;

a link member connecting the pivot means of the two braces and maintaining a substantially constant distance between said pivot means when the lower member is rotated relative to the upper member, so that the gear means of the two members also remain engaged when rotated about the pivot means in order to rotate the brace members relative to each other; and means for securing the upper and lower brace members respectively to a person's thigh and leg, said pivot means of the members being anterior to the knee joint of the person when said two brace members are so secured and when the person and the brace members are viewed in profile, so that the rotation of the lower brace member tracks the movement of the tibia in flexion and so that the link member and portions of the brace members remain close to the knee joint when it is bent to provide greater support and protection of the knee joint, wherein the lower brace member is a substantially flat plate and the upper member a plate, wherein said pivot means of the upper member is at one end of the upper member, wherein the other end of the upper member for engaging the thigh of a person is at an angle to the plane of the lower plate defining a dihedral angle, so that pistoning forces on a knee are reduced, wherein said dihedral angle is approximately 10°.

* * * * *